(12) United States Patent
Montgomery et al.

(10) Patent No.: US 11,605,282 B2
(45) Date of Patent: Mar. 14, 2023

(54) SYSTEM AND METHOD OF PREDICTING OXYGEN LEVEL DESATURATION

(71) Applicant: Covidien LP, Mansfield, MA (US)

(72) Inventors: Dean Montgomery, Edinburgh (GB); Paul S. Addison, Edinburgh (GB); Andre Antunes, Edinburgh (GB)

(73) Assignee: Covidien LP, Mansfield, MA (US)

( * ) Notice: Subject to any disclaimer, the term of this patent is extended or adjusted under 35 U.S.C. 154(b) by 274 days.

(21) Appl. No.: 16/838,989

(22) Filed: Apr. 2, 2020

(65) Prior Publication Data
US 2021/0312781 A1 Oct. 7, 2021

(51) Int. Cl.
*G08B 21/04* (2006.01)
*A61B 5/0205* (2006.01)
(Continued)

(52) U.S. Cl.
CPC ........ *G08B 21/0453* (2013.01); *A61B 5/0205* (2013.01); *A61B 5/14551* (2013.01);
(Continued)

(58) Field of Classification Search
CPC ... A61B 5/0205; A61B 5/021; A61B 5/02416; A61B 5/0816; A61B 5/14542; A61B 5/14551; A61B 5/7221; A61B 5/7246; A61B 5/7264; A61B 5/7267; A61B 5/7275; A61B 5/746; G06N 3/04; G06N 3/08; G08B 21/0453; G16H 50/20
See application file for complete search history.

(56) References Cited

U.S. PATENT DOCUMENTS

2018/0310893 A1    11/2018   Everman et al.
2021/0022660 A1*    1/2021   Quinn ................... A61B 5/389

OTHER PUBLICATIONS

EiMoaqet, Hisham et al., "Evaluating Preditcions of Critical Oxygen Desaturation Events," Physiological Measurement, Institute of Physics Publishing, Bristol, GB, vol. 35, No. 4, Mar. 12, 2014, pp. 639-655.*

(Continued)

*Primary Examiner* — Toan N Pham
*Assistant Examiner* — Rajsheed O Black-Childress
(74) *Attorney, Agent, or Firm* — Holzer Patel Drennan

(57) ABSTRACT

Implementations described herein disclose a method of determining how well predictions of an impending hypoxia are reported in real-time, so that a user has higher confidence in the reported predictions. Specifically, the method of predicting oxygen level desaturation disclosed herein includes generating an input sequence of oxygen levels based on an input signal sequence, the input signals indicative of a physiological condition of a patient, generating an input feature sequence based on at least one of the input signal sequence and the input sequence of oxygen levels, generating, using a neural network, a predicted value sequence of the oxygen levels based on the input feature sequence, comparing the predicted value sequence of the oxygen levels with the input sequence of oxygen levels for a predetermined temporal window to generate a predicted sequence confidence value, and generating, in response to determining that the predicted sequence confidence value is above a threshold confidence value, an oxygen level desaturation prediction based on the predicted value sequence.

18 Claims, 7 Drawing Sheets

(51) Int. Cl.
*A61B 5/1455* (2006.01)
*A61B 5/00* (2006.01)
*G06N 3/08* (2006.01)
*G06N 3/04* (2006.01)
*G08B 21/18* (2006.01)
*A61B 5/024* (2006.01)

(52) U.S. Cl.
CPC .......... *A61B 5/7221* (2013.01); *A61B 5/7267* (2013.01); *A61B 5/7275* (2013.01); *A61B 5/746* (2013.01); *G06N 3/04* (2013.01); *G06N 3/08* (2013.01); *G08B 21/182* (2013.01); *A61B 5/02416* (2013.01)

(56) References Cited

OTHER PUBLICATIONS

Mahuli, Amita P. et al., "Prediction of Photoplethysmogram Signals Using Sequential ELM," 2016 International Joint Conference on Neural Networks (IJCNN), IEEE, Jul. 24, 2016, pp. 1977-1984.*
Sutskever, et al., "Sequence to Sequence Learning with Neural Networks," Neural Information Processing Systems Conference, 2014.
International Search Report and Written Opinion dated Jul. 7, 2021 in related PCT Application No. PCT/US2021/024796, 17 pages.

* cited by examiner

SYSTEM AND METHOD OF PREDICTING OXYGEN LEVEL DESATURATION

BACKGROUND

Biomedical monitoring devices such as pulse oximeters, glucose sensors, electrocardiograms, capnometers, fetal monitors, electromyograms, electroencephalograms, ultrasounds, etc., may provide lagging indicators of physiological phenomena. In other words, these devices generally provide a signal or a series of signals that are indicative of a patient condition that has already occurred. For example, a pulse oximeter is a small, clip-like device that attaches to a body part, like toes or an earlobe. It's most commonly put on a finger to measure how well a patient's heart is pumping oxygen through the body by determining the oxygen content of arterial blood. However, while the oxygen level provides an indication of various conditions such as hypoxemia, low cardiac output, tissue perfusion issues, oxygen saturation levels determined by a pulse oximeter is a lagging indicator that may be indicative of the physiological condition causing such saturation level.

SUMMARY

Implementations described herein disclose a method of determining how well predictions of an impending hypoxia are reported in real-time, so that a user has higher confidence in the reported predictions. Specifically, the method of predicting oxygen level desaturation disclosed herein includes generating an input sequence of oxygen levels based on an input signal sequence, the input signals indicative of a physiological condition of a patient, generating an input feature sequence based on at least one of the input signal sequence and the input sequence of oxygen levels, generating, using a neural network, a predicted value sequence of the oxygen levels based on the input feature sequence, comparing the predicted value sequence of the oxygen levels with the input sequence of oxygen levels for a predetermined temporal window to generate a predicted sequence confidence value, and generating, in response to determining that the predicted sequence confidence value is above a threshold confidence value, an oxygen level desaturation prediction based on the predicted value sequence.

In one implementation, the sequence of input signal includes one or more of a sequence of $SpO_2$ level values, heart rate, a percentage modulation derived from a photoplethysmographic (ppg) signal, and a pulse amplitude derived from the ppg signal. Alternatively, comparing the predicted value sequence with the input signal sequence for a predetermined temporal window may further comprise generating a metric value is indicative of confidence in the predicted value sequence. In another implementation, the metric value is indicative of confidence in the predicted value sequence may be a root mean square error (RMSE) value based on the predicted value sequence and the input value sequence during the predetermined window.

In an alternative implementation, generating the oxygen level desaturation prediction further comprising comparing the predicted value sequence to a threshold value to generate the oxygen level desaturation prediction. An implementation of the method further includes selecting the threshold level based on the predicted sequence confidence value and generating an alarm based on a combination of the predicted sequence confidence value and a predicted value of the oxygen level. Another implementation of the method further includes selecting the time period in the future when an alarm is generated based on the predicted sequence confidence value and allowing a user to select an alarm sensitivity level and generating an alarm based on the selected alarm sensitivity level and a value of the predicted sequence confidence value. In an alternative implementation, the predicted sequence confidence value is a root-mean-square-deviation (RMSD) of an input $SpO_2$ signal sequence and a predicted $SpO_2$ value sequence during a comparison time window.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Other implementations are also described and recited herein.

BRIEF DESCRIPTIONS OF THE DRAWINGS

A further understanding of the nature and advantages of the present technology may be realized by reference to the figures, which are described in the remaining portion of the specification.

DETAILED DESCRIPTIONS

Hypoxemia is a condition that indicates lower than normal concentration of oxygen levels in arterial blood of a patient. Hypoxemia may result in hypoxia or hypoxic condition for the patient, characterized by inadequate oxygen content in patient tissues. Pulse oximeters may be used to measure the oxygen content of arterial blood to indicate existing hypoxia condition as well as to predict impending hypoxia. A clinician may want to be alerted when oxygen saturation level in arterial blood dips, indicating an oxygen level desaturation. However, a pulse oximeter is a lagging indicator in that the oxygen level desaturation has already occurred before the device is able to detect the desaturation event or to inform the clinician. If the pulse oximeter is able to predict impending desaturations, then the clinician may be able to take pre-emptive action to prevent the desaturation or to mitigate its effects. The technology disclosed herein provides a method for verifying an output of a model predicting an impending hypoxia or oxygen level desaturation. Specifically, a method disclosed herein allows determining how well a prediction of impending hypoxia may be performing in real-time, so as to provide higher confidence in the reported predictions.

Figure 1:
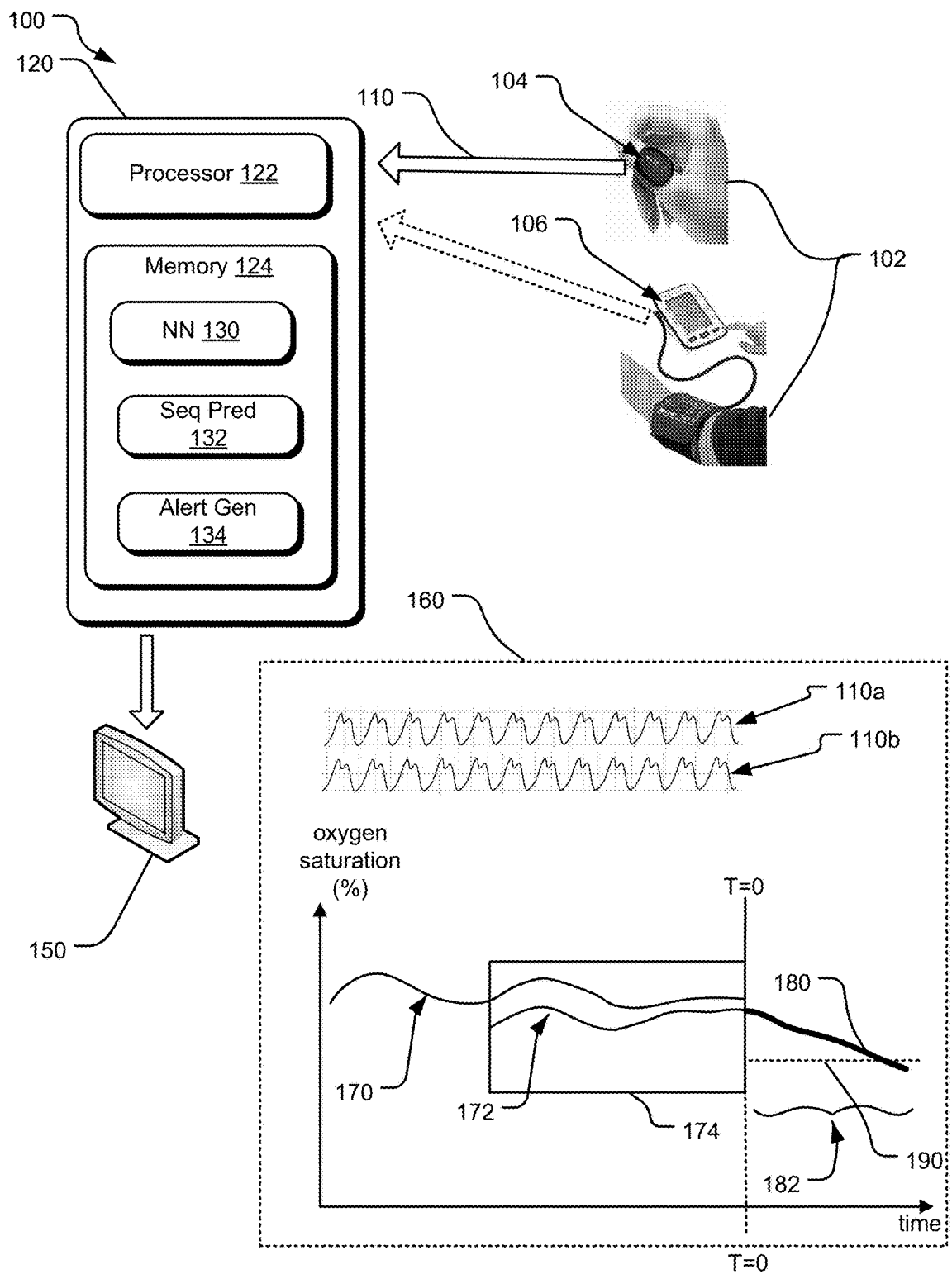
FIG. 1 illustrates an example schematic view of oxygen level desaturation prediction system for a patient as disclosed herein.

FIG. 1 illustrates an example schematic view of oxygen level desaturation prediction system 100 for a patient 102 as disclosed herein. A pulse oximeter 104 may be used to measure the oxygen saturation ($SpO_2$) level in the patient. For example, the pulse oximeter 104 may be attached to the patient's thumb. The pulse oximeter 104 may be communicatively connected to a computing system 120. For example, the pulse oximeter 104 may be connected to the computing system 120 wirelessly and it may send a sequence of signals measured by the oximeter 104 over a period of time. For example, such input signal sequence 110 may be communicated at every second. In one implementation, the input signal sequence 110 may include photoplethysmographic (PPG) signals such as a red signal 110a, an infrared signal 110b, etc. The pulse oximeter 104 may use the values of the red signal 110a and the infrared signal 110b, to generate values of oxygen saturation levels (the $SpO_2$ levels). A sequence of such $SpO_2$ levels generated by the pulse oximeter 104 is illustrated by an input $SpO_2$ signal sequence 170.

The computing device 120 may be a computing system that includes a microprocessor 122, a memory 124, and various other components. An example of such a computing system 120 is disclosed in FIG. 7 below. In a method disclosed herein, the memory 124 may be used to store the sequence of $SpO_2$ signals generated by the pulse oximeter 104. Furthermore, the memory 124 may also store one or more instructions of a neural network module 130 that can be executed using the micro-processor 122 to analyze the sequence of $SpO_2$ signals generated by the pulse oximeter 104 to generate a predicted $SpO_2$ value sequence based on the input signal sequence 110 and the input $SpO_2$ signal sequence 170.

In one implementation the neural network module 130 may be a deep neural network module that analyzes the input sequence of $SpO_2$ signal using a long short-term memory (LSTM) based layers to generate the predicted $SpO_2$ value sequence. The deep neural network module may be configured to generate a predicted $SpO_2$ value sequence for a time-window in the future, such as a 15 seconds time-window, a 30 seconds time window, a one-minute time window, etc. Specifically, the neural network module 130 may be configured so that the predicted $SpO_2$ value sequence overlaps in time with the past $SpO_2$ levels as indicated by the input sequence of $SpO_2$ signals.

Such overlap between the input sequence of $SpO_2$ signals and the predicted $SpO_2$ value is disclosed by the graph 160 in FIG. 1. Specifically, the graph 160 includes the input $SpO_2$ signal sequence 170 and a predicted $SpO_2$ value sequence 172. As illustrated the sequences 170 and 172 overlap in time during a comparison time window 174. In one implementation, various input features may be developed based on the input signal sequence 110, the input $SpO_2$ signal sequence 170, or the combination thereof. A sequence of such input features may be input to the neural network module 130. The neural network module 130 may generate the predicted $SpO_2$ value sequence 172 based on an input matrix including various sequences of such input features. Example sequence of input features maybe a sequence of values generated as combination of $SpO_2$ levels, PPG signals, percentage modulation, pulse amplitude, maximum upslope of the pulse, location of pulse maximum, location of maximum in first derivative, pulse period, heart rate, etc.

The memory 124 may also include various instructions for implementing a sequence to sequence prediction module 132. The sequence to sequence prediction module 132 may be configured to compare the input $SpO_2$ signal sequence 170 and the predicted $SpO_2$ value sequence 172 over the comparison time window 174. In one implementation, the comparison time window 174 ends at the present time (T=0). Thus, the sequence to sequence prediction module 132 compares the input $SpO_2$ signal sequence 170 and the predicted $SpO_2$ value sequence 172 in the comparison time window 174 before the present time (T=0). A future portion 180 of the predicted $SpO_2$ value sequence 172 for a future time period 182 (beyond the time T=0) is indicated in FIG. 1 by a darker line.

Furthermore, the sequence to sequence prediction module 132 may also generate, based on the comparison of the values of the input $SpO_2$ signal sequence 170 and the predicted $SpO_2$ value sequence 172, a metric that is indicative of confidence in the output of the neural network module 130. For example, such metric may indicate a level of match between the input $SpO_2$ signal sequence 170 and the predicted $SpO_2$ value sequence 172 in the comparison time window 174. If the values are a poor match in the comparison time window 174, the metric may indicate that a lower confidence in the predicted $SpO_2$ value sequence 172. In such case, the future portion 180 of the predicted values of the $SpO_2$ 172 in the future period 182 are ignored.

The metric value indicative of the level of match between the input $SpO_2$ signal sequence 170 and the predicted $SpO_2$ value sequence 172 in the comparison time window 174 may be quantified as a root mean square error (RMSE) value that is given as follows:

$$RMSE = \sqrt{\frac{\sum_{i=0}^{N}(x_i - y_i)^{2^2}}{N}}$$  Equation 1

Here $x_i$ are the signal point values from the input $SpO_2$ signal sequence 170 contained within comparison time window 174 and $y_i$ are the signal point values from the predicted $SpO_2$ value sequence 172 contained within comparison time window 174. N is the number of sample points in the comparison time window 174. In this case, the magnitude of the RMSE value provides an indication of the match. Thus, a large value of RMSE is indicative of a large discrepancy between the input $SpO_2$ signal sequence 170 and the predicted $SpO_2$ value sequence 172, whereas a smaller value of the RMSE is indicative of a better match between the input $SpO_2$ signal sequence 170 and the predicted $SpO_2$ value sequence 172. Thus, the RMSE value may be used as a predicted sequence confidence value (PSCV) that indicates the confidence in the predicted $SpO_2$ value sequence 172. Alternatively, other measurements or calculations generated based on the input $SpO_2$ signal sequence 170 and the predicted $SpO_2$ value sequence 172 may also be used as PSCV. For example, in one implementation a mean absolute percentage error (MAPE) value, calculated based on the input $SpO_2$ signal sequence 170 and the predicted $SpO_2$ value sequence 172, may be used at the PSCV. Yet alternatively, mean square error (MSE), mean absolute error (MAE), median absolute deviation (MAD), correlation coefficient (R) between the input $SpO_2$ signal sequence 170 and the predicted SpO$_2$ value sequence 172, etc., or any combination of such measures may be used as PSCV.

The memory 124 may also have an alert generation module 134 that is configured to generate an alert signal based on evaluation of the metric, such as the RMSE, and the value of the predicted SpO$_2$ as indicated by the predicted SpO$_2$ value sequence 172. For example, in one implementation, the alert generation module 134 compares the value of the value of the predicted SpO$_2$ as indicated by the predicted SpO$_2$ value sequence 172 to a threshold 190 and any time the value of the predicted SpO$_2$ as indicated by the predicted SpO$_2$ value sequence 172 drops below the threshold value 190, an alert indicating desaturation is generated. For example, the threshold value 190 may be selected to be 90% predicted SpO$_2$. In such as case, if any value of the future portion 180 of the predicted SpO$_2$ value sequence 172 is expected to be at or below 90%, an alarm signal is generated. Alternatively, the alarm signal is generated based on combination of the levels of the future portion 180 of the predicted SpO$_2$ value sequence 172 as compared to the threshold value 190 and the PSCV. For example, if any part of the future portion 180 of the predicted SpO$_2$ value sequence 172 falls below 82.5% with PSCV of 95, the alarm generation module 134 may cause a triggering of the alarm. On the other hand, when the PSCV value is 20, indicating very little confidence, even if the value of any part of the future portion 180 of the predicted SpO$_2$ value sequence 172 is below 80%, it may not cause the alarm generation module 134 to trigger the alarm. In yet another implementation, any part of the future portion 180 of the predicted SpO$_2$ value sequence 172 being below 90% may trigger the alarm when the PSCV, as defined by the RMSE, is between +/−3%.

In another implementation, the threshold value 190 may be selected based on the PSCV. Thus, if the PSCV is higher, indicating higher confidence in the predictions, a lower threshold value 190 may be selected. On the other hand, if the PSCV is lower, indicating lower confidence level, a higher threshold value 190 may be selected to ensure that an expected desaturation incident is not overlooked.

In another implementation, the RMSE value as per Equation 1 above may be used to determine the confidence in the future portion 180 of the predicted values of the SpO$_2$ 172. Thus, the larger the RMSE, the lower the confidence in the future portion 180 of the predicted values of the SpO$_2$ 172. If there is a high confidence of a hypoxemic event, as indicated by lower RMSE value, then an alarm may be sounded sooner if the value of the future portion 180 of the predicted values of the SpO$_2$ 172 indicates a desaturation level indicative of hypoxemia.

In one implementation, the alarm generation module 134 may provide an alarm level user interface (UI) to a user that allows the user to control how readily the alarm is generated in response to the SpO$_2$ level predictions. For example, such alarm level UI may allow the user to set alarm based on a continuous scale or at a number of discrete levels. For example, a high sensitivity level for the alarm may correspond to a root-mean-square-deviation (RMSE) of the input SpO$_2$ signal sequence 170 and a predicted SpO$_2$ value sequence 172 during the comparison time window 174 to be 3%. Thus, the high sensitivity level indicates high sensitivity when higher error rate, as indicated by higher RMSD, is permitted. Similarly, a low sensitivity level for the alarm may correspond to a root-mean-square-deviation (RMSE) of the input SpO$_2$ signal sequence 170 and a predicted SpO$_2$ value sequence 172 during the comparison time window 174 to be 1%. Here the low sensitivity level indicates low sensitivity when lower error rate, as indicated by lower RMSD, is permitted.

In an alternative implementation, other devices that measure the patient's other physiological parameters may be also be used with the oxygen level desaturation prediction system 100. For example, a blood pressure monitor 106 may be used to monitor the blood pressure level and communicate a sequence of blood pressure level signals to the computing device 120. In such an implementation, various methods and modules disclosed herein for predicting the impending oxygen desaturation level may also be used to predict impending changes in blood pressure. Similarly, these methods and modules may also be used for predicting changes in other physiological signals collected by other devices, such as a heart rhythm monitor, a pulse monitor, a cardiac monitor, a regional oxygen saturation monitor, a brain monitor, a respiration monitor, etc. Other examples of input signals may be percentage modulation, pulse amplitude, maximum upslope of the pulse, location of pulse maximum, location of maximum in first derivative, pulse period, SpO$_2$ value, heart rate, or some other variables derived from a photoplethysmographic (PPG) signal and/or the PPG red/infra-red signals themselves.

Figure 2:
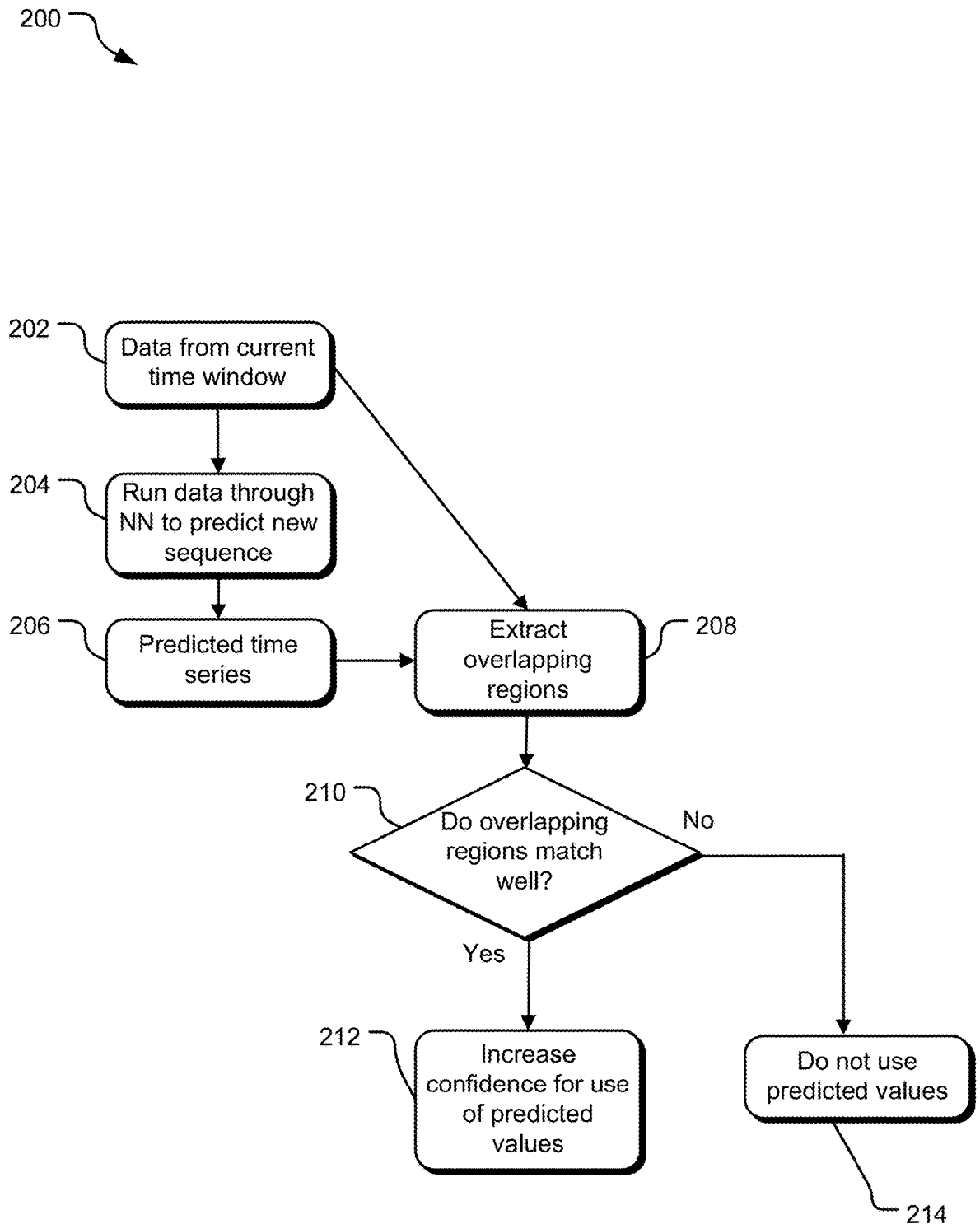
FIG. 2 illustrates example operations for predicting oxygen level desaturation based on sequence to sequence comparison using a neural network.

FIG. 2 illustrates operations 200 for predicting oxygen level desaturation based on sequence to sequence comparison using a neural network. Specifically, an operation 202 collects data related to a patient from a current time window. For example, such data may be SpO$_2$ levels for the patient collected from an oximeter, patient heart rate, etc. The input data may be stored in an input time series vector. In one implementation, the operation 204 may generate a matrix of various input feature sequences, where the input feature sequences are developed based on the input data. At operation 204, the input data and/or the input feature matrix are run through a neural network to generate a sequence of predicted values. The predicted values are stored at an operation 206 in a predicted time series vector.

An operation 208 takes the input time series vector and the predicted time series vectors and extracts data for an overlapping region, such as the time during the comparison time window 174 disclosed in FIG. 1. Subsequently, an operation 210 determines if the values of the input time series vector and the predicted time series vector during the overlapping regions match each other. Such determination regarding the match may be made by calculating an RMSE value between the input time series vector and the predicted time series vector. If the operation 210 determines that there is a good match between the input time series vector and the predicted time series vector, for example, based on the value of the RMSE being below a threshold, an operation 212 increases the confidence attributed to the predicted time series vector so that values of a future portion of the predicted time series vector, such as values of the time series vector beyond time T=0, may be used to manage alarms. However, if the operation 210 determines that the input time series vector and the predicted time series vector do not match well, no predicted value is output at an operation 214. In an implementation, if the operation 210 determines that the input time series vector and the predicted time series vector do not match well, the confidence attributed to the predicted time series vector is lowered.

Figure 3:
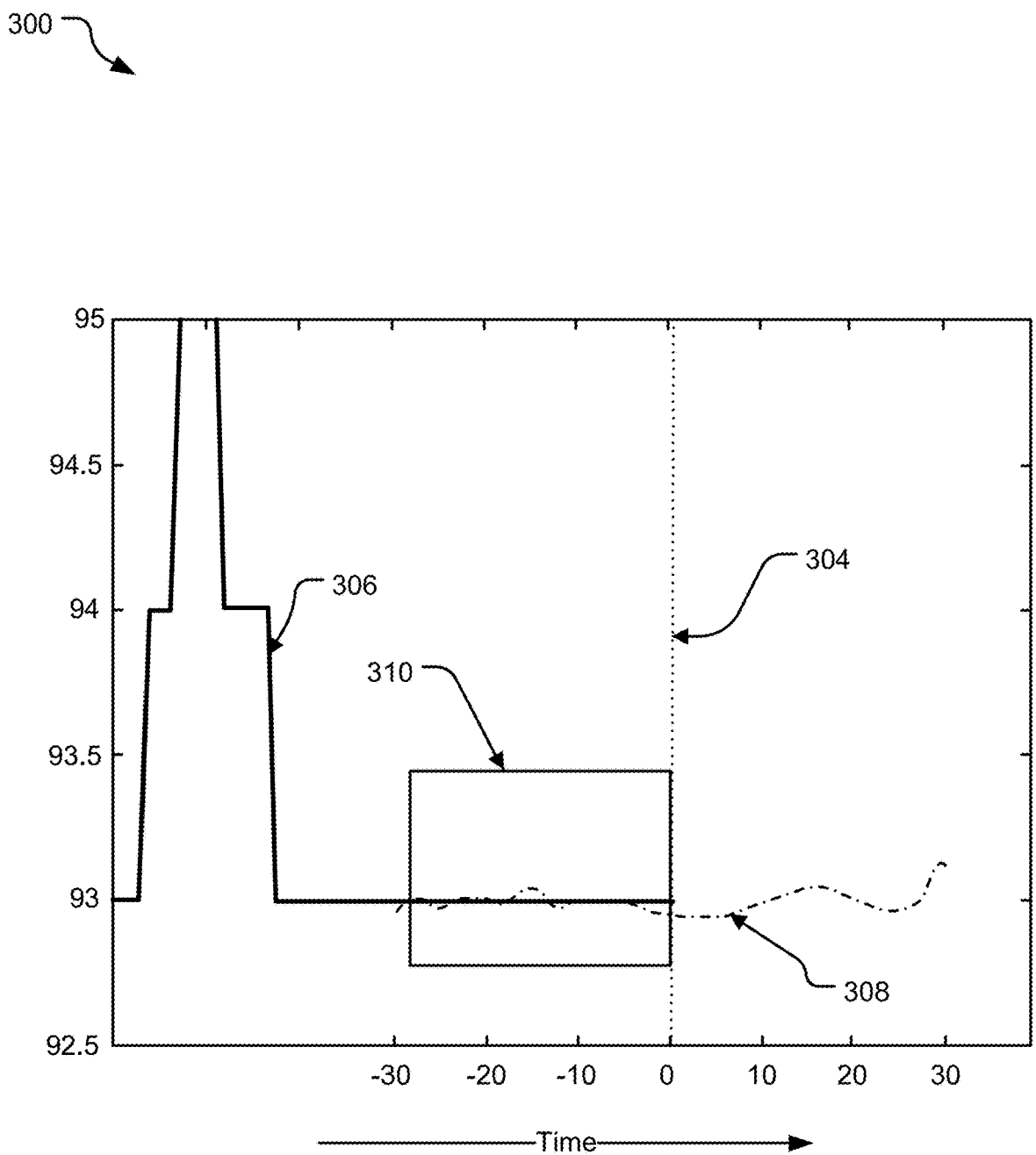
FIG. 3 illustrates an example graph indicating a good match between an input data time series and a predicted data time series.

FIG. 3 illustrates a graph 300 indicating a good match between an input data time series 306 and a predicted data time series 308. Input data, e.g. percentage modulation, pulse amplitude, maximum upslope of the pulse, location of pulse maximum, location of maximum in first derivative, pulse period, SpO$_2$ value, heart rate as described above, may be input to a neural network to generate a predicted data series 308. In one implementation, various features generated from the input data are input to the neural network model to generate the predicted data series 308. The input data time series 306 and the predicted data time series 308 are compared in a window 310 before time zero, as indicated by 304, to determine if there is a good match between them. If there is a good match, as seen in FIG. 3, a higher confidence value is attributed to the values of future portion of the predicted data time series 308, such as the values beyond time zero, as indicated by 304. In this case an alarm may be generated based on values of such future portion of the predicted data time series 308.

Figure 4:
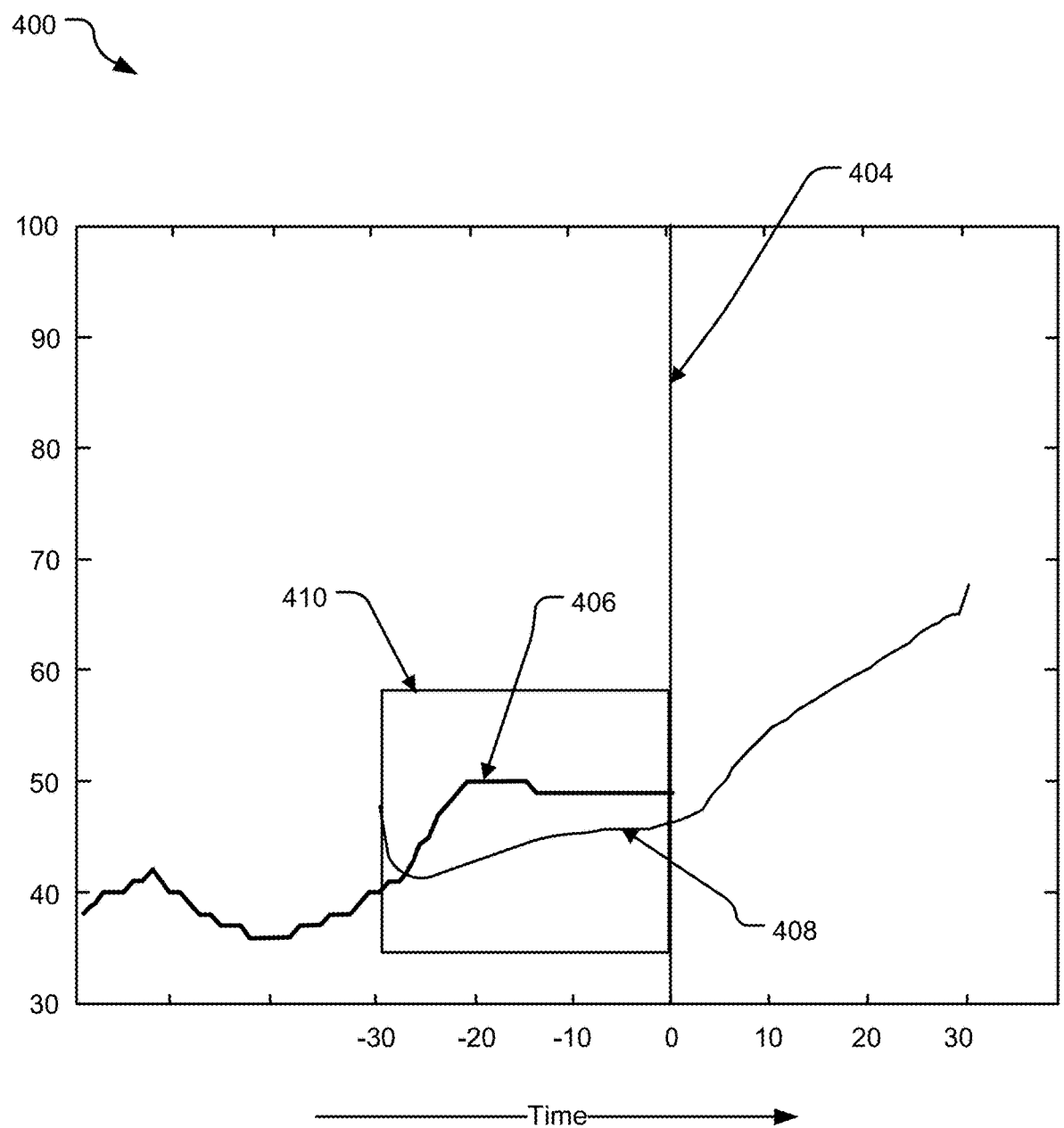
FIG. 4 illustrates an example graph indicating a poor match between an input data time series and a predicted data time series.

FIG. 4 illustrates a graph 400 indicating a poor match between an input data time series 406 and a predicted time series 408. Specifically, the input data time series 406 may be used to generate the predicted series 408. Alternatively, one or more feature vectors generated from the input data time series 406 may also be used by a neural network module to generate the predicted time series 408. The input data time series 406 and the predicted time series 408 are compared in an overlapping region 410 before time zero, as indicated by 404, to determine if there is a good match between them. As seen in FIG. 4, the input data time series 406 does not closely match the predicted time series 408 inside the overlapping region 410, which may be manifested by a higher RMSE value. As a result, a lower confidence value is attributed to the values of future portion of the predicted time series 408, such as the values beyond time zero, indicated by 404. In this case no alarm may be generated based on values of such predicted time series 408.

In one implementation, the neural network module 130 disclosed in FIG. 1 may include multiple neural network models where each of such multiple models are trained in a different manner. For example, the length of time-period for each of such multiple neural network models may be selected to be different. Alternatively, the initial conditions for each of the multiple neural network models may be selected to be different from each other. Alternatively, each of these multiple neural network models may have a different architecture. For example, such models may include a convolutional neural network, a modular neural network, a recurrent neural network, a feed-forward neural network, etc. Yet alternatively, the number of layers used for each of the multiple neural network models may be different from each other.

Figure 5:
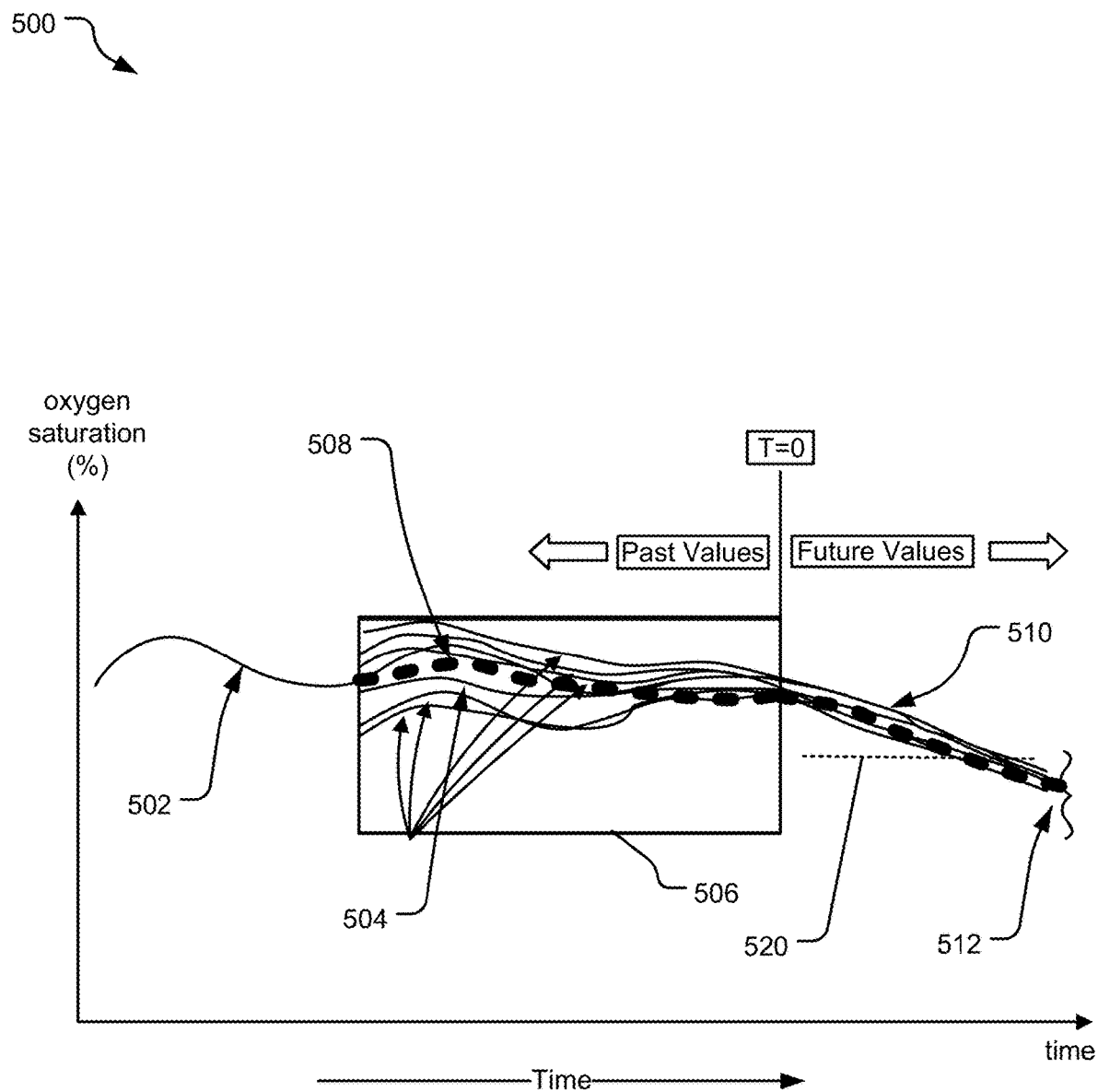
FIG. 5 illustrates an example graph where multiple neural network models are used to generate multiple predicted $SpO_2$ value sequences.

FIG. 5 illustrates an example graph where multiple neural network models are used to generate multiple predicted SpO$_2$ value sequences 504 during a comparison time window 506 before time T=0. Each of such predicted SpO$_2$ value sequences 504 also includes future sections that extend beyond time T=0. In such implementation, an aggregate predicted SpO$_2$ value sequence 508 (illustrated by a bold dashed line) may be generated based on some combination of the multiple predicted SpO$_2$ value sequences 504. For example, such combination may be a mean, a median, a weighted mean, etc., of the multiple predicted SpO$_2$ value sequences 504.

In one implementation, the multiple predicted SpO$_2$ value sequences 504 may be generated by slightly modifying the values of the input features to the neural network model by adding a random perturbation. Thus, an input feature sequence 502 may be configured to have a distribution that is stochastically modified by the addition of a random perturbation. For example, an input feature sequence 502 that is a combination of amplitude A and heart rate (HR) from the IR/Red signals may be modified as A+distribution (A) and HR+distribution (HR) before it is input to the neural network. An example distribution function may be a normal distribution function. Alternatively, the distribution function may be fine-tuned based on the selection of the neural network model or based on characteristics of the training data.

The measure of confidence in a future section of the predicted value of SpO$_2$ 510 may also be based on a measure of the distribution 512 of the predicted value of SpO$_2$ 510. For example, if the predicted values of SpO$_2$ 510 includes 100 sequences and at least 80 of these sequences indicate a future value below a threshold saturation level 520, an alarm is generated to indicate potential hypoxemic event. Alternatively, other measures, such as standard deviation, interquartile range, etc., that are generated based on the predicted values of SpO$_2$ 510 may be compared to the threshold level 520 to generate the alarm.

Figure 6:
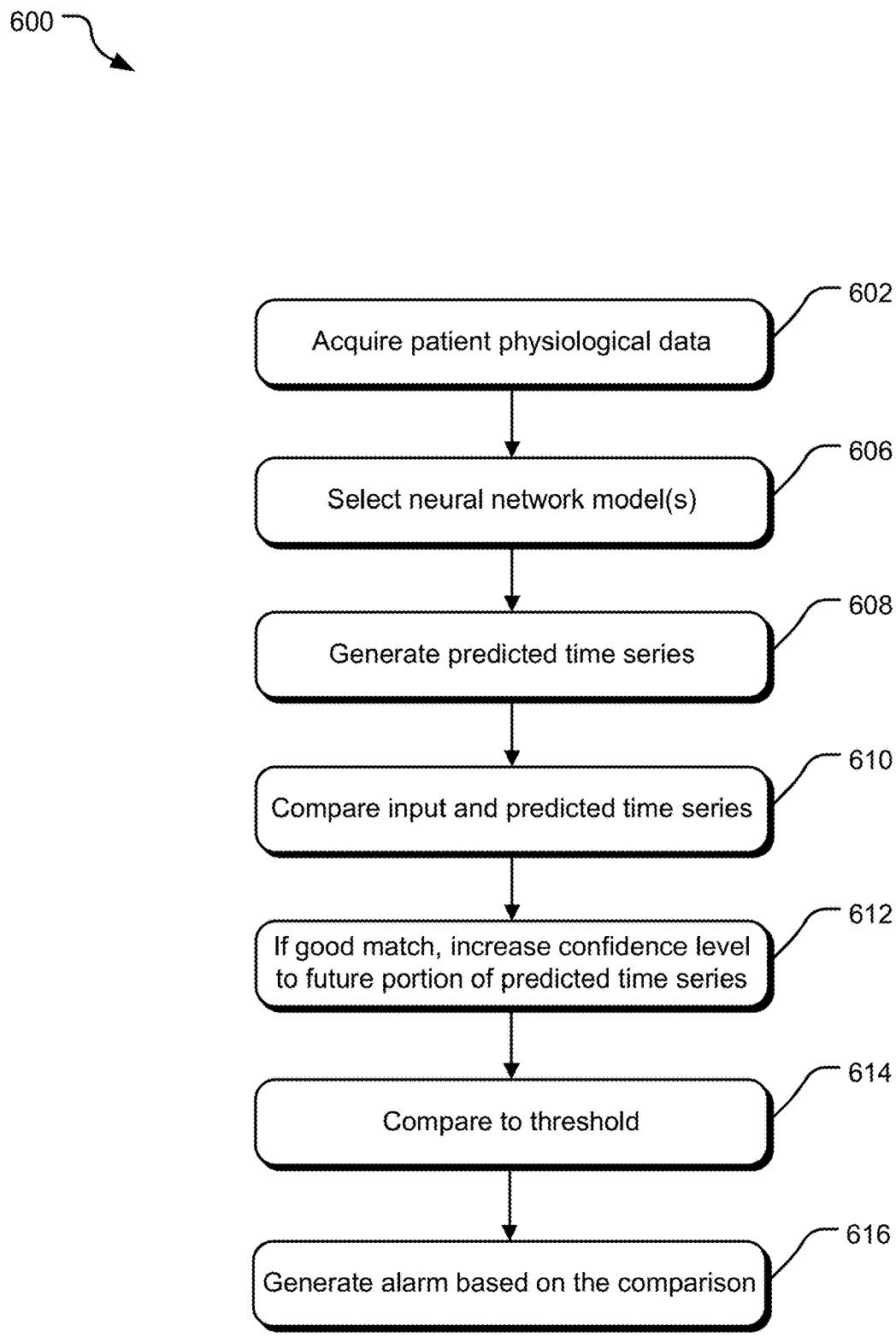
FIG. 6 illustrates alternative example operations for the oxygen level desaturation prediction system disclosed herein.

FIG. 6 illustrates operations 600 for the oxygen level desaturation prediction system disclosed herein. An operation 602 acquires a patient's physiological data as the input data. This input data may include PPG signals, percentage modulation, pulse amplitude, maximum upslope of the pulse, location of pulse maximum, location of maximum in first derivative, pulse period, SpO$_2$ value, heart rate, as described above, etc. An operation 606 selects a neural network model that may be used to generate the predicted time series from the input data. In one implementation, more than one neural network models may be used and the input time series may be fed to each one of the selected models. Alternatively, slightly different versions of the input time series may be input to each of the several selected neural network models.

An operation 608 generates a predicted time series as an output of the selected neural network model. If more than one neural network is used, the output of the various neural networks may be combined to generate a combined predicted time series. An operation 610 compares the input time series and the predicted time series during a comparison time window (such as the comparison time window 174 discussed in FIG. 1) to determine if there is a good match between the input time series and the predicted time series. For example, such comparison may be made by calculating an RMSE or other predicted sequence confidence value based on the values of the input time series and the predicted time series during a comparison time window.

If there is a good match as indicated by the predicted sequence confidence value, an operation 612 increases a confidence level allocated to a future portion of the predicted time series (such as the future portion 180 of the predicted SpO$_2$ value sequence 172 disclosed in FIG. 1). The values of the predicted time series for the future period beyond the comparison window may be compared to a threshold value by an operation 614 and based on the comparison an alarm may be generated by an operation 616.

Figure 7:
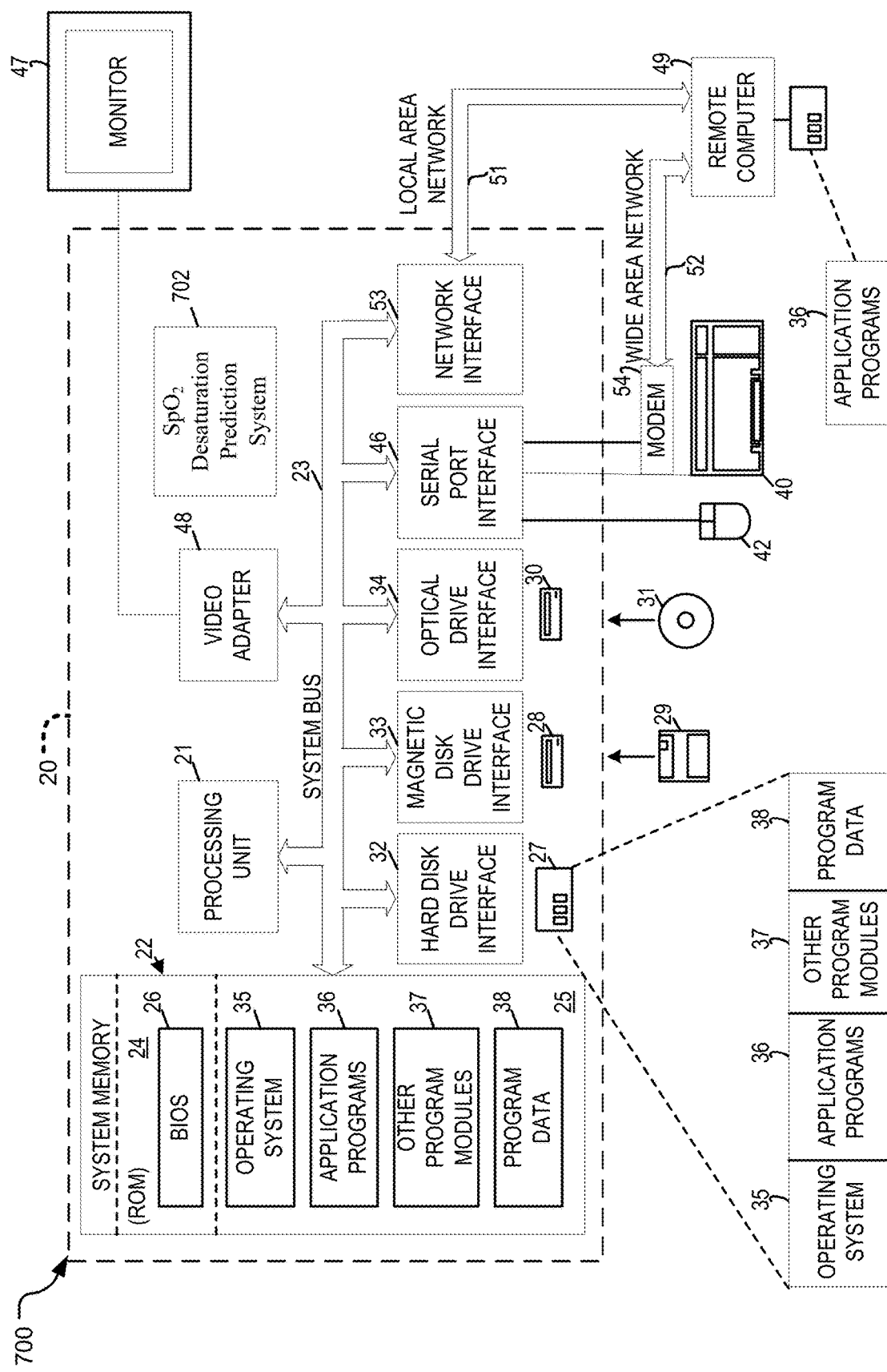
FIG. 7 illustrates an example computing system that may be useful in implementing the described technology.

FIG. 7 illustrates an example system 700 that may be useful in implementing the described technology for providing attestable and destructible device identity. The example hardware and operating environment of FIG. 7 for implementing the described technology includes a computing device, such as a general-purpose computing device in the form of a computer 20, a mobile telephone, a personal data assistant (PDA), a tablet, smart watch, gaming remote, or other type of computing device. In the implementation of FIG. 7, for example, the computer 20 includes a processing unit 21, a system memory 22, and a system bus 23 that operatively couples various system components including the system memory to the processing unit 21. There may be only one or there may be more than one processing unit 21, such that the processor of the computer 20 comprises a single central-processing unit (CPU), or a plurality of processing units, commonly referred to as a parallel processing environment. The computer 20 may be a conventional computer, a distributed computer, or any other type of computer; the implementations are not so limited.

The system bus 23 may be any of several types of bus structures including a memory bus or memory controller, a peripheral bus, a switched fabric, point-to-point connections, and a local bus using any of a variety of bus architectures. The system memory may also be referred to as simply the memory, and includes read only memory (ROM) 24 and random-access memory (RAM) 25. A basic input/output system (BIOS) 26, containing the basic routines that help to transfer information between elements within the computer 20, such as during start-up, is stored in ROM 24. The computer 20 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated tangible computer-readable media provide non-volatile storage of computer-readable instructions, data structures, program modules and other data for the computer 20. It should be appreciated by those skilled in the art that any type of tangible computer-readable media may be used in the example operating environment.

A number of program modules may be stored on the hard disk drive 27, magnetic disk 28, optical disk 30, ROM 24, or RAM 25, including an operating system 35, one or more application programs 36, other program modules 37, and program data 38. A user may generate reminders on the personal computer 20 through input devices such as a keyboard 40 and pointing device 42. Other input devices (not shown) may include a microphone (e.g., for voice input), a camera (e.g., for a natural user interface (NUI)), a joystick, a game pad, a satellite dish, a scanner, or the like. These and other input devices are often connected to the processing unit 21 through a serial port interface 46 that is coupled to the system bus 23, but may be connected by other interfaces, such as a parallel port, game port, or a universal serial bus (USB) (not shown). A monitor 47 or other type of display device is also connected to the system bus 23 via an interface, such as a video adapter 48. In addition to the monitor, computers typically include other peripheral output devices (not shown), such as speakers and printers.

The computer 20 may operate in a networked environment using logical connections to one or more remote computers, such as remote computer 49. These logical connections are achieved by a communication device coupled to or a part of the computer 20; the implementations are not limited to a particular type of communications device. The remote computer 49 may be another computer, a server, a router, a network PC, a client, a peer device or other common network node, and typically includes many or all of the elements described above relative to the computer 20. The logical connections depicted in FIG. 7 include a local-area network (LAN) 51 and a wide-area network (WAN) 52. Such networking environments are commonplace in office networks, enterprise-wide computer networks, intranets and the Internet, which are all types of networks.

When used in a LAN-networking environment, the computer 20 is connected to the local network 51 through a network interface or adapter 53, which is one type of communications device. When used in a WAN-networking environment, the computer 20 typically includes a modem 54, a network adapter, a type of communications device, or any other type of communications device for establishing communications over the wide area network 52. The modem 54, which may be internal or external, is connected to the system bus 23 via the serial port interface 46. In a networked environment, program engines depicted relative to the personal computer 20, or portions thereof, may be stored in the remote memory storage device. It is appreciated that the network connections shown are examples and other means of communications devices for establishing a communications link between the computers may be used.

In an example implementation, software or firmware instructions for providing attestable and destructible device identity may be stored in memory 22 and/or storage devices 29 or 31 and processed by the processing unit 21. One or more datastores disclosed herein may be stored in memory 22 and/or storage devices 29 or 31 as persistent datastores. For example, an $SpO_2$ desaturation prediction system 702 (illustrated within the personal computer 20) may be implemented on the computer 20 (alternatively, the $SpO_2$ desaturation prediction system 702 may be implemented on a server or in a cloud environment). The $SpO_2$ desaturation prediction system 702 may utilize one of more of the processing unit 21, the memory 22, the system bus 23, and other components of the personal computer 20.

In contrast to tangible computer-readable storage media, intangible computer-readable communication signals may embody computer readable instructions, data structures, program modules or other data resident in a modulated data signal, such as a carrier wave or other signal transport mechanism. The term "modulated data signal" means a signal that has one or more of its characteristics set or changed in such a manner as to encode information in the signal. By way of example, and not limitation, intangible communication signals include wired media such as a wired network or direct-wired connection, and wireless media such as acoustic, RF, infrared and other wireless media.

The implementations described herein are implemented as logical steps in one or more computer systems. The logical operations may be implemented (1) as a sequence of processor-implemented steps executing in one or more computer systems and (2) as interconnected machine or circuit modules within one or more computer systems. The implementation is a matter of choice, dependent on the performance requirements of the computer system being utilized. Accordingly, the logical operations making up the implementations described herein are referred to variously as operations, steps, objects, or modules. Furthermore, it should be understood that logical operations may be performed in any order, unless explicitly claimed otherwise or a specific order is inherently necessitated by the claim language.

The above specification, examples, and data provide a complete description of the structure and use of exemplary embodiments of the invention. Since many implementations of the invention can be made without departing from the spirit and scope of the invention, the invention resides in the claims hereinafter appended. Furthermore, structural features of the different embodiments may be combined in yet another implementation without departing from the recited claims.

What is claimed is:

1. A method of predicting oxygen level desaturation, comprising:

generating an input sequence of oxygen levels based on an input signal sequence, the input signals indicative of a physiological condition of a patient;

generating an input feature sequence based on at least one of the input signal sequence and the input sequence of oxygen levels;

generating, using a neural network, a predicted value sequence of the oxygen levels based on the input feature sequence;

comparing the predicted value sequence of the oxygen levels with the input sequence of oxygen levels for a predetermined temporal window to generate a predicted sequence confidence value;

generating, in response to determining that the predicted sequence confidence value is above a threshold confidence value, an oxygen level desaturation prediction based on the predicted value sequence; and generating an alarm based on a combination of (a) the predicted sequence confidence value and (b) comparison of the oxygen level desaturation prediction over a future time period to a threshold oxygen level.

2. The method of claim 1, wherein the sequence of input signal includes one or more of a sequence of $SpO_2$ level values, heart rate, a percentage modulation derived from a photoplethysmographic (ppg) signal, and a pulse amplitude derived from the ppg signal.

3. The method of claim 1, wherein comparing the predicted value sequence with the input signal sequence for a predetermined temporal window may further comprise generating a metric value is indicative of confidence in the predicted value sequence.

4. The method of claim 3, wherein the metric value is indicative of confidence in the predicted value sequence may be a root mean square error (RMSE) value based on the predicted value sequence and the input value sequence during the predetermined window.

5. The method of claim 1, wherein generating the oxygen level desaturation prediction further comprising comparing the predicted value sequence to the threshold oxygen level to generate the oxygen level desaturation prediction.

6. The method of claim 5, further comprising selecting the threshold oxygen level based on the predicted sequence confidence value.

7. The method of claim 5, further comprising selecting the time period in the future when an alarm is generated based on the predicted sequence confidence value.

8. The method of claim 5, further comprising allowing a user to select an alarm sensitivity level and generating an alarm based on the selected alarm sensitivity level and a value of the predicted sequence confidence value.

9. The method of claim 8, wherein the predicted sequence confidence value is a root-mean-square-deviation (RMSD) of an input $SpO_2$ signal sequence and a predicted $SpO_2$ value sequence during a comparison time window.

10. In a computing environment, a method performed at least in part on at least one processor, the method comprising:

generating an input sequence of oxygen levels based on an input signal sequence, the input signals indicative of a physiological condition of a patient;

generating an input feature sequence based on the input signal sequence and the input sequence of oxygen levels;

generating, using a neural network, a predicted value sequence of the oxygen levels based on the input feature sequence;

comparing the predicted value sequence of the oxygen levels with the input sequence of oxygen levels for a predetermined temporal window to generate a predicted sequence confidence value;

generating, in response to determining that the predicted sequence confidence value is above a threshold confidence value, an oxygen level desaturation prediction value based on the predicted value sequence; and generating an alarm based on a combination of (a) the predicted sequence confidence value and (b) comparison of the oxygen level desaturation prediction value over a future time period to a threshold oxygen level.

11. The method of claim 10, wherein the predicted sequence confidence value is a root mean square error (RMSE) value based on the predicted value sequence and the input value sequence during the predetermined window.

12. The method of claim 10, further comprising selecting the threshold oxygen level based on the predicted sequence confidence value.

13. The method of claim 10, further comprising selecting the time period in the future when an alarm is generated based on the predicted sequence confidence value.

14. The method of claim 10, wherein generating the predicted value sequence for the oxygen levels based on the input signal sequence further comprising:

inputting the sequence of input signals to a plurality of neural networks; and generating, using the plurality of neural networks, a plurality of predicted value sequences for the oxygen levels based on the input signal sequence.

15. The method of claim 14, further comprising modifying the predicted sequence confidence value based on dispersion of the plurality of predicted value sequences.

16. A physical article of manufacture including one or more tangible computer-readable storage media, encoding computer-executable instructions for executing on a computer system a computer process to provide an automated connection to a collaboration event for a computing device, the computer process comprising:

generating, using a neural network, a predicted value sequence for oxygen levels based on an input signal sequence of a patient's $SpO_2$ level values;

comparing the predicted value sequence with the input signal sequence for a predetermined temporal window to generate a predicted sequence confidence value;

generating, in response to determining that the predicted sequence confidence value is above a threshold confidence value, an oxygen level desaturation prediction based on the predicted value sequence; and generating an alarm based on a combination of (a) the predicted sequence confidence value and (b) comparison of the oxygen level desaturation prediction over a future time period to a threshold oxygen level.

17. The physical article of manufacture of claim 16, wherein the computer process further comprising comparing the oxygen level prediction sequence with a threshold oxygen level to generate an alarm.

18. The physical article of manufacture of claim 16, wherein the threshold oxygen level is selected based on the predicted sequence confidence value.

* * * * *